United States Patent [19]

Alvarez

[11] Patent Number: 5,895,749
[45] Date of Patent: Apr. 20, 1999

[54] MALE FERTILITY AND CONTRACEPTION HOME TEST KITS

[75] Inventor: Juan G. Alvarez, Boston, Mass.

[73] Assignee: Beth Israel Deaconess Medical Center, Boston, Mass.

[21] Appl. No.: 08/332,825

[22] Filed: Oct. 31, 1994

[51] Int. Cl.[6] .................... G01N 33/573; G01N 33/537; G01N 33/543
[52] U.S. Cl. .................... 435/7.4; 435/2; 435/7.94; 435/25; 435/28; 435/806; 435/975; 436/518; 436/538; 436/906; 436/175; 436/177
[58] Field of Search .................... 435/2, 7.4, 7.94, 435/25, 28, 806, 975; 436/510, 65, 814, 906, 518, 538, 175, 177

[56] References Cited

U.S. PATENT DOCUMENTS

| | | | |
|---|---|---|---|
| 4,007,087 | 2/1977 | Ericsson et al. | 195/1.8 |
| 4,009,260 | 2/1977 | Ericsson et al. | 424/105 |
| 4,804,537 | 2/1989 | Bergman et al. | 424/105 |
| 4,945,044 | 7/1990 | Huszar | 435/17 |
| 5,068,089 | 11/1991 | Ericsson et al. | 422/61 |
| 5,219,729 | 6/1993 | Hodgen | 435/7.21 |
| 5,434,057 | 7/1995 | Dorian | 435/18 |

FOREIGN PATENT DOCUMENTS

| | | |
|---|---|---|
| 2 539 628 | 7/1984 | France . |
| 2 709 250 | 3/1995 | France . |
| 87/02382 | 4/1987 | WIPO . |

OTHER PUBLICATIONS

Alvarez, J.G., Pavlou, S.N., Lasso, J.L., Saragovie, H.U. "Selection of Subsets of Human Spermatozoa (HS) with Increased Motile Lifetimes (MLT) By Solid Phase Immunoadsorption" *Journal of Andrology*. Jan./Feb. 1993 Supplement p. P–65; Abstract 170.

R.J. Aitken, "Relationship Between Iron–Catalyzed Lipid Peroxidation Potential and Human Sperm Function". *J. Reprod. Fertil.* (1993), 98(1), 257–65.

Schill, W.B., "Indications For Determination of Acrosin Activity", *Andrologia*, (1986) 18(5), 548–52.

Crabbe. M.J.C. "The Development of A Qualitative Assay For Male Infertility From A Study of Enzymes in Human Semen", *J. Reprod. Fertil.* (1977), 51(1), 73–6.

R.J. Aitken, "Relationship Between Iron–Catalyzed Lipid Peroxidation Potential and Human Sperm Function", *Chemical Abstracts* (1993), vol. 119, No. 11, abstract No. 114355.

Schill, W.B., "Indications For Determination of Acrosin Activity", *Chemical Abstracts*, (1987) vol. 106, No. 3, abstract No. 16572.

Crabbe, M.J.C. "The Development of A Qualitative Assay For Male Infertility From A Study of Enzymes in Human Semen", *Chemical Abstracts* (1977), vol. 87, No. 25, abstract No. 198648.

J.G. Alvarez, D. Minaretzis, J.F. Mortola and I.E. Thompson, Dept. of Ob&Gyn/Boston IVF, Beth Israel Hospital, Harvard Medical School, Boston, MA. Sperm Stress Test: A Novel Test that Predicts Pregnancy Outcome in Assisted Reproductive Technologies (Art),. Abstract Form from *The American Fertility Society 50th Annual Meeting*, Nov. 5–10, 1994 (mailed Oct. 5, 1994).

J.G. Alvarez, M.M. Alper, S.P. Oskowitz, E. Sullivan and J. Mortola, Dept. of Ob&Gyn/Boston IVF, Beth Israel Hospital, Harvard Medical School, Boston, MA (Spon: B. Sachs). "Superoxide Dismutase Activity in Human Sperm Correlates with Pregnancy Rate after In Vitro Fertilization", P103, Scientific Abstracts, 246 (mailed in Mar. 94).

Juan G. Alvarez, Joseph C. Touchstone, Luis Blasco and Bayard T. Storey, "Spontaneous Lipid Peroxidation and Production of Hydrogen Peroxide and Superoxide in Human Spermatozoa—Superoxide Dismutase as Major Enzyme Protectant Against Oxygen Toxicity", *Journal of Andrology*, vol. 8, No. 5, pp. 338–348, (Sep./Oct. 1987).

Gabor Huszar and Lynne Vigue, "Correlation Between the Rate of Lipid Peroxidation and Cellular Maturity as Measured by Creatine Kinase Activity in Human Spermatozoa", *Journal of Andrology*, vol. 15, No. 1, pp. 71–77 (Jan./Feb. 1994).

Juan G. Alvarez and Bayard T. Storey, "Evidence for Increased Lipid Peroxidative Damage and Loss of Superoxide Dismutase Activity as a Mode of Sublethal Cryodamage to Human Sperm During Cryopreservation", *Journal of Andrology*, vol. 13, No. 3, pp. 232–241 (May/Jun. 1992).

Juan G. Alvarez and Bayard T. Storey, "Evidence that Membrane Stress Contributes More than Lipid Peroxidation to Sublethal Cryodamage in Cryopreserved Human Sperm: Glycerol and other Polyols as Sole Cryoprotectant", *Journal of Andrology*, vol. 14, No. 3, pp. 199–209.

Juan G. Alvarez, Jaime L. Lasso, Luis Blasco, Rocio C. Nunez, Susan Heyner, Pedro P. Caballero and Bayard T. Storey, "Centrifugation of Human Spermatozoa Induces Sublethal Damage; Separation of Human Spermatozoa from Seminal Plasma by a Dextran Swim–up Procedure without Centriguation Extends their Motile Lifetime", *Human Reproduction*, vol. 8, No. 7, pp. 1087–1092 (1993).

Lasso et al., 1994. Mechanism of superoxide dismutase loss from human sperm cells during cryopreservation. J. Androl. 15: 255–65.

Aitken et al, 1989. Generation of Reactive Oxygen Species, Lipid Peroxidation, and Human Sperm Function. Biol. Reprod. 40: 183–197.

Aitken et al, 1994. Reactive Oxygen Species Generation and Human Spermatozoa: The Balance of Benefit and Risk. BioEssays 16: 259–267.

*Primary Examiner*—James C. Housel
*Assistant Examiner*—James L. Grun
*Attorney, Agent, or Firm*—Lahive & Cockfield, LLP

[57] ABSTRACT

Kits and assays, incorporating antibodies specific for glutathione peroxidase, for determining the fertilizing ability of a male at home or in a clinical laboratory are disclosed.

6 Claims, No Drawings

MALE FERTILITY AND CONTRACEPTION HOME TEST KITS

GOVERNMENT SUPPORT

The work resulting in this invention was supported in part by National Institute of Health Grant Nos. RO1-HD-31584-01 and RO1-HD-15842-09. The U.S. Government may therefore be entitled to certain rights in the invention.

BACKGROUND OF THE INVENTION

According to recent studies, male infertility is responsible almost 40% of the time that a couple is unable to conceive a child. By convention, male infertility is diagnosed based on low sperm motility and/or count. When no sperm are observed to move in a sample obtained from a male, that male is diagnosed as being infertile. However, besides zero motility, there are really no motility thresholds for distinguishing fertile sperm from infertile sperm. With regard to sperm count, twenty million sperm per milliliter or greater is generally considered to be in the fertile range. Sperm count and motility can be assessed using commercially available instruments, such as computerized videoanalysis systems.

U.S. Pat. No. 5,068,089 describes a home kit for testing fertility of human sperm, based on ability of the sperm to reduce a dye. The extent of reduction (displayed calorimetrically), is said to be indicative of sperm fertilizing ability. However, this test is complicated to perform, requires incubation at a temperature above room temperature and does not distinguish between reduction due to sperm cells or other cells, which may be present in a semen sample.

U.S. Pat. No. 5,219,729 describes a laboratory assay for determining the fertilizing ability of sperm based on the affinity of binding between to a oocyte zona pellucida fragment. The tighter the binding, the greater the fertilizing ability of the sperm sample. However, this assay requires freshly prepared oocyte fragments and at least four hour's time during which the sperm must be kept in contact with the oocyte fragment.

A simple and rapid assay for determining the pregnancy potential of sperm in a laboratory or at home is needed.

SUMMARY OF THE INVENTION

In one aspect, the invention features assays for determining the pregnancy potential of sperm samples based on measuring an indicator of lipid peroxidation. The sample can simultaneously be assayed for sperm count to ensure that the lipid peroxidation results are due to sperm and not contaminating cells that may be present in the sample. A preferred method for determining sperm count is by measuring the concentration of glutathione peroxidase (GpX) in a sperm sample.

In a preferred embodiment for home use, the indicator of sperm lipid peroxidation is sperm superoxide dismutase (SOD) activity. In a particularly preferred embodiment, sperm SOD activity is determined based on detecting a detectably labeled SOD antibody and the sperm GpX concentration is determined by detecting a detectably labeled GpX antibody. The concentrations of SOD and/or GpX obtained can be compared against known values to determine the pregnancy potential or contraceptive ability of the sperm sample. In an especially preferred embodiment for home use, the SOD and/or GpX antibody is calorimetrically labeled and the results obtained in a particular fertility assay are compared to various color possibilities indicated on a chart provided with the kit.

In another aspect, the invention features kits for determining the pregnancy potential of a sperm sample. In general, a kit can comprise a number of simple components which can be packaged in a box. The components can include: i) containers; ii) reagents for performing sperm lipid peroxidation assays and/or sperm count assays; iii) means for determining lipid peroxidation and/or sperm count; and iv) means for determining the pregnancy potential of a sperm sample (e.g. based on comparison with a standard). The kit may also optionally include: a means for removing contaminants from a semen sample (e.g. swim-up or percoll gradient); means for liquefying the semen sample (e.g. $\alpha$-chymotrypsin or $\alpha$-amylase); and dispensing devices for measuring and/or dispensing reagents.

In a preferred embodiment, the means for detecting sperm lipid peroxidation is based on sperm superoxide dismutase (SOD) activity and/or the means for detecting sperm count is based on sperm glutathione peroxidase (GpX) concentration. In a particularly preferred embodiment, the means for detecting sperm SOD activity employs a calorimetrically labeled SOD antibody and the means for detecting sperm GpX concentration employs a calorimetrically labeled GpX antibody. The kit also preferably includes instructions and a color chart against which concentrations of SOD and/or GpX can be compared against known values.

A instant disclosed kits and methods can be performed by most anyone in about 20 minutes' time. The kits and methods provide information which is useful, for example, for monitoring the impact of changes in factors such as diet, sleep, exercise, exposure to smoke or other carcinogens, and intake of alcohol or drugs on the fertility of sperm samples produced thereafter. In addition, the kits and methods can indicate whether a particular fertility treatment has been effective. Based on the results obtained, the kits can provide information as to whether sperm subsequently obtained from the same male will initiate a pregnancy upon contact with an oocyte. Other features and advantages of the assays and kits will become readily apparent from the following Detailed Description and Claims.

DETAILED DESCRIPTION

In general, the invention relates to methods and kits for determining the pregnancy potential of a sperm sample. Sperm with "high pregnancy potential" as described herein have a greater than 50% probability for initiating a pregnancy upon contact with an oocyte. Although high fertility sperm have an increased probability of initiating a pregnancy, contact of high fertility sperm with an oocyte does not guarantee a successful pregnancy. Other factors, such as inability of an oocyte to decondense human sperm chromatin, defective oocyte DNA (e.g. due to age), two-cell embryo block or early embryo demise, may prevent the initiation of a pregnancy even where sperm with high pregnancy potential is employed.

Sperm with low pregnancy potential (contraceptive ability), on the other hand, has very little or no chance of initiating a pregnancy upon contact with an oocyte. Indication that a sperm sample provided by a particular male has low pregnancy potential indicates that subsequent sperm samples will also have contraceptive ability. However, because the fertility of a male's sperm can change over time and can be influenced by such factors as diet, sleep, exercise, exposure to smoke or other carcinogens, or intake of alcohol or drugs, the fertility results obtained for a particular sperm sample are in general only accurate for a period of about 48 hours.

Preferred sperm samples for use in the disclosed assays are obtained from a human or animal (e.g. a bull, stallion, ram or other domesticated animal or an endangered animal). To ensure accuracy, tests are preferably performed on freshly collected ejaculate.

Preferred tests for determining the pregnancy potential or contraceptive ability of a sperm sample are lipid peroxidation tests, which measure an indicator of lipid peroxidation or a change in an indicator resulting from lipid peroxidation over a period of time under defined conditions. The value obtained is then compared with a standard value for that particular indicator to determine the pregnancy potential of that sperm sample.

One type of lipid peroxidation test measures change of an indicator of lipid peroxidation (e.g. motility or lipid peroxidation breakdown products), over a period of time in response to a stress (a stress test). A stress test (ST) score can be obtained by dividing a measured post-stress value of an indicator of lipid peroxidation by a measured pre-stress value. Examples of appropriate stresses or stressing agents for obtaining a stress test score include radiation (such as thermal (e.g. as described in Example 4), electric or magnetic), freeze-thawing, oxidation or exposure to chemical agents (e.g. oxidizing agents such as the ferrous iron/ascorbate system described in Example 5). When motility is used as an indicator of lipid peroxidation and the stress is thermal, a stress test score of greater than about 0.5 indicates high pregnancy potential.

In a preferred embodiment for home use, the indicator of sperm lipid peroxidation is based on sperm superoxide dismutase (SOD) activity. As shown in Example 1, sperm samples with SOD activities greater than about $9U/10^8$ cells have been shown to be associated with high pregnancy rates after IVF, while activities less than about $7U/10^8$ cells are associated with low pregnancy rates. In a particularly preferred embodiment for identifying sperm with high pregnancy potential at home, sperm SOD activity is tested based on detection of a colorimetrically labeled SOD antibody.

To ensure that the SOD activity is due to sperm and not other cells that may be present in a sample, sperm glutathione peroxidase (GpX) or another constant sperm cell marker is measured. GpX remains at a constant level in all sperm cells. Consequently, a determination of the concentration of GpX in a particular sperm sample provides an indication of the number of sperm in that sample. In fact, as shown in Example 2, detection of GpX alone is useful for identifying sperm samples with low fertilizing or contraceptive ability.

As described in Example 3, the concentrations of SOD and/or GpX obtained can be compared against known values to determine whether the sperm in the sample has high pregnancy potential. In an especially preferred embodiment for home use, the SOD and/or GpX antibody is calorimetrically labeled and the results obtained in a particular fertility assay are compared to various color possibilities indicated on a chart provided with the kit.

Other indicators of lipid peroxidation that can be used in performing a lipid peroxidation test include:

Lipid peroxidation breakdown products Samples that have a relatively high post-stress value of lipid peroxidation breakdown products (such as lipid hydroperoxides, malonaldehyde, pentane and ethane) relative to pre-stress value (ST scores <0.5) do not result in successful pregnancies, while ST scores of about 0.5 or greater increase the rate of initiating a pregnancy. The lipids can be analyzed spectrophotometrically. For example, lipid hydroperoxides can be extracted with hexane and detected at 233 nm. Malonaldehyde can be measured at 532 nm following reaction with the thiobarbituric acid (Tapel, A. L. et al., (1959) *Arch Biochem Biophys*, 80:326). Pentane and ethane can be measured by gas chromatography.

Ratio of membrane phospholipids Samples that oxidize at high rates have phosphatidylethanolamine (PE)/phosphatidylcholine (PC) ratios <0.5, while samples that oxidize at low rates (ST scores >0.8 as indicated by loss of motility) have PE/PC ratios of greater than about 0.7. Therefore, sperm with pregnancy potential have PE/PC ratios greater than about 0.7, but less than about 1.5, sperm with some pregnancy potential have PE/PC ratios of greater than about 0.5 and less than about 0.5, and sperm with low pregnancy potential have PE/PC ratios of less than about 0.5. PE and PC can be measured by high-performance thin-layer chromatography (Alvarez, J. G. et al., (1987) *J Liquid Chromatogr* 10: 3557)

Oxidation of DNA Samples that oxidize at high rates have higher levels of oxo-8-deoxyguanosine ($oxo^8dG$), which can be measured, for example, by high pressure liquid chromatography (HPLC) using electrochemical detection (Fraga, C. G. et al., (1991) *Proc Natl Acad Sci* 88:11003.). Sperm with high pregnancy potential have less than about 20 fmol of $oxo^8dG/\mu g$ of DNA, while sperm with low pregnancy potential have greater than about 40 mol of $oxo^8dG/\mu g$ of DNA.

Superoxide dismutase (SOD) activity Solid phase-bound anti Cu/Zn-SOD antibodies and enzyme labeled anti-Cu/Zn-SOD antibodies can be used to detect SOD activity as described in Example 3. Sperm samples with SOD activities greater than about $9U/10^8$ cells have been shown to be associated with high pregnancy rates after IVF, while activities less than about $7U/10^8$ cells are associated with low pregnancy rates.

Surface SOD immunofluorescence Samples that oxidize at high rates have low surface-SOD immunofluorescence and low total SOD activity. Surface-SOD immunofluorescence can be measured by flow cytometry using sheep anti-Cu/Zn-SOD IgG polyclonal antibodies and FITC-conjugated rabbit anti-sheep secondary antibodies (Alvarez, J. G. 18th Annual Meeting American Andrology Society, Tampa, Fla., 1993, abstract 170). Greater than about 300 FITC units is indicative of high pregnancy potential, while less than about 300 FITC units is indicative of low pregnancy potential.

Ratio of unsaturated fatty acids to saturated fatty acids Unsaturated fatty acids are prone to oxidation while saturated fatty acids are insensitive to this process. Determination of the ratio of the unsaturated fatty acid, docosahexaenoic acid (22:6) to the saturated fatty acid palmitic acid (16:0) or of other unsaturated fatty acids to saturated fatty acids can be used to predict pregnancy potential. Samples that oxidize at high rates will have low docosahexaenoic acid/palmitic acid ratios. Unsaturated/saturated fatty acids can be measured by gas chromatography following alkaline methanolysis with 1N sodium methoxide at 40° C. for 1 hour (Alvarez, J. G. and J. C. Touchstone, Practical Manual on Lipid Analysis. Series of Monographs: I—Fatty Acids. Norell Press (New Jersey), 1991). A ratio of unsaturated to saturated fatty acids of greater than or equal to about 0.6 indicates high pregnancy potential, while a ratio of less than about 0.5 indicates low pregnancy potential.

Creatine kinase activity The concentration of creatine kinase in sperm reflects the degree of cytoplasmic extrusion during the last phase of spermatogenesis. Samples exhibiting abnormally high levels of creatine kinase activity have also been found to have high rates of lipid peroxidation as determined by the PE/PC ratios (PE/PC ratios <0.5). This correlation supports the detection of creatine kinase activity as a means for determining pregnancy potential of a sperm sample. Creatine kinase activity in human sperm can be measured by spectrophotometric analysis at 365 nm of the NADPH generated during reaction of creatine kinase with ADP to produce creatine and ATP, followed by reaction of hexokinase with ATP and glucose to produce glucose-6-phosphate, followed by reaction of glucose-6-phosphate dehydrogenase with glucose-6-phosphate and NADP to produce NADPH. The NADPH generated under these conditions is proportional to the activity of creatine kinase in human sperm (Huszar, G. (1988) *Gamete Res* 19:67,). Creatine kinase (CK) exists in two isoforms: MM and BB. Sperm with high pregnancy potential have a CK–MM/CK–MM+CK–BB ratio of greater than or equal to about 10%.

Reagents used in assays to determine the pregnancy potential of sperm can be packaged with required containers and instructions and be sold as a kit for home or clinical laboratory use. In general, a kit can comprise a number of simple components which can be packaged in a box. In general, the kit can include: i) containers; ii) reagents for performing sperm lipid peroxidation assays and/or sperm count assays; iii) means for determining lipid peroxidation and/or sperm count; and means for determining the pregnancy potential of a sperm sample. A suitable kit may also optionally include: a means for removing contaminants from a semen sample (e.g. based on swim-up, Alvarez, J. G. et al., Human Reproduction 8:1087–1092 (1993); percoll gradient, or centrifugation).

A preferred kit for home determination of sperm pregnancy potential can include: i) a collection container (optionally conformed to capture ejaculate, and/or containing a solution (e.g. enzymatic) that facilitates semen liquefaction); ii) a first container (optionally containing a sugar solution and/or isotonic solution to facilitate sperm swim-up); iii) a dispensing device (e.g. pipet) for delivering a defined volume of semen from the collection tube into the first container; iv) a second container which includes a means for detecting sperm lipid peroxidation and/or sperm count (e.g. direct visual indication or aided by spectrophotometry, flow cytometry, chromatography etc.); iv) a dispensing device (e.g. pipet) for delivering a defined volume of semen from the first container into the second container; and v) means for determining the pregnancy potential of a sperm sample (e.g. based on comparison with a standard).

In a preferred embodiment, the means for detecting sperm lipid peroxidation is based on sperm superoxide dismutase (SOD) activity and/or the means for detecting sperm count is based on sperm glutathione peroxidase (GpX) concentration. In a particularly preferred embodiment, the means for detecting sperm SOD activity employs a calorimetrically labeled SOD antibody and the means for detecting sperm GpX concentration employs a calorimetrically labeled GpX antibody. The kit also preferably includes a color chart against which concentrations of SOD and/or GpX can be compared against known values. The kit can be optimized to develop color based on the GPx levels corresponding to sperm concentrations greater than or equal to about 200,000. Since sperm recoveries obtained using the swim-up described, range between 8 and 12% with a mean value of 10±2.1%, the cut-off for the color reaction can be adjusted to correspond to 10 million motile cells per milliliter of semen, which is the threshold established for normospermic semen.

A preferred kit for home determination of contraceptive sperm can include: i) a collection container (optionally conformed to capture ejaculate, and/or containing a solution (e.g. enzymatic) that facilitates semen liquefaction); ii) a first container (optionally containing a sugar solution and/or isotonic solution to facilitate sperm swim-up); iii) a dispensing device (e.g. pipet) for delivering a defined volume of semen from the collection tube into the first container; iv) a second container which includes a means for detecting sperm count (e.g. direct visual indication or aided by spectrophotometry, flow cytometry, chromatography etc.); iv) a dispensing device (e.g. pipet) for delivering a defined volume of semen from the first container into the second container; and v) means for determining the sperm count and thereby the contraceptive capacity of a sperm sample (e.g. based on comparison with a standard). Indication of less than 10,000 motile sperm indicates contraceptive capacity.

The present invention is further illustrated by the following Examples which are intended merely to further illustrate and should not be construed as limiting. The entire contents of all of the references (including literature references, issued patents, published patent applications, and co-pending patent applications) cited throughout this application are hereby expressly incorporated by reference.

EXAMPLE 1

Superoxide Dismutase (SOD) Activity in Sperm Correlates with Pregnancy Rate

Human spermatozoa (HS) release oxygen radicals and undergo spontaneous lipid peroxidation (SLP) resulting in extensive damage to the sperm plasma and acrosomal membranes and loss of their pregnancy potential. Cu/Zn-superoxide dismutase (SOD) protects HS against oxygen radical-mediated toxicity and SLP and that surface SOD immunoreactivity is expressed over the midpiece and postequatorial regions of HS (Alvarez and Storey, (1992) *J. Andrology* 13(3):232–241, the contents of which are incorporated herein by reference).

Whether SOD activity correlates with sperm pregnancy potential and pregnancy rate was studied using HS samples obtained from 27 male partners from couples undergoing in vitro fertilization (IVF). The age of the female partner ranged from 24 to 49 years. The number of oocytes inseminated ranged from 3 to 20 and the number of embryos transferred from 1 to 7. HS samples were washed using the standard mini Percoll procedure, and resuspended in HTF medium containing 10% plasmanate. An aliquot of the HS suspension was utilized for IVF and another aliquot was used to measure the SOD activity of that particular sample using solid phase-bound anti Cu/Zn-SOD antibodies and enzyme labeled anti-Cu/Zn-SOD antibodies to bind to the SOD antibody complex (The Binding Site Inc., 5889 Oberlin Drive, San Diego, Calif. 92121).

SOD activity in the HS samples examined ranged from 1.5 to 12 U/$10^8$ cells (p<0.001). All six HS samples with SOD activities less than or equal to 3.3U/$10^8$ cells resulted in failed fertilization (p<0.001). Between 4.7 and 7.1U/$10^8$ cells, fifteen out of sixteen oocytes were fertilized but no ongoing pregnancies resulted.

These results show that HS samples with high SOD activity (i.e. greater than or equal to about 7 units/$10^8$ cells) have a high pregnancy potential, while samples with low SOD activity (i.e. less than about 7 units/$10^8$ cells) have a low pregnancy potential.

EXAMPLE 2

Male Contraceptive Home Kit

The ejaculate is collected in a tube containing 5 mg/mL of chymotrypsin in an isotonic solution. After about three minutes (at which time most sperm should be liquefied), an aliquot (about 0.5 mls) of the liquefied semen is added to a test tube containing 20 mg/ml of a dextran solution (tube #1), so that the total solution in the test tube reaches the black mark indicated on the tube. The tube is then gently mixed (e.g. by tapping) and overlaid with an isotonic solution (about 0.5 mls.) so that the total solution in the test tube reaches the red mark indicated on the tube.

The tube is allowed to stand for about five minutes at room temperature, so that the motile sperm cells swim-up to the upper layer. A fraction of the solution between the black and red marks is then obtained and added to a second test tube (tube #2), which contains peroxidase-conjugated anti-glutathione peroxidase (GPx) IgG polyclonal antibodies (The Binding Site, Inc., 5889 Oberlin Drive, San Diego, Calif. 92121) dissolved in a hypotonic solution. After five minutes, a dip test strip with anti-human GPx IgG polyclonal antibodies (The Binding Site, Inc., 5889 Oberlin Drive, San Diego, Calif. 92121) are inserted into test tube #2. After five minutes, the test strip is removed from the tube and rinsed with tap water.

The test strip is then dipped into a third test tube (tube #3), which contains the peroxidase substrate, hydrogen peroxide ($H_2O_2$) and diaminobenzidine (DAB) (Sigma Chemical Co., St. Louis, Mo. 63178). After about 5 minutes, the calorimetric result obtained is compared to various color possibilities indicated on a chart provided with the kit. Color in the GPx pad indicates greater than 10,000 motile sperm/mL, indicating a fertile male. The lack of color indicates an infertile male.

EXAMPLE 3

Sperm Pregnancy Potential Home Kit

The ejaculate is collected in a tube containing 5mg/mL of chymotrypsin in an isotonic solution. After about three minutes (at which time most sperm should be liquefied), an aliquot (about 0.5 mls.) of the liquefied semen is added to a test tube containing 20 mg/ml of a dextran solution (tube #1), so that the total solution in the test tube reaches the black mark indicated on the tube. The tube is then gently mixed (e.g. by tapping) and overlaid with an isotonic solution (about 0.5 mls.), so that the total solution in the test tube reaches the red mark indicated on the tube.

The tube is allowed to stand for about five minutes at room temperature, so that the motile sperm cells swim-up to the upper layer. A fraction of the solution between the black and red marks is than obtained and added to a second test tube (tube #2), which contains peroxidase-conjugated superoxide dismutase (SOD) (The Binding Site, Inc., 5889 Oberlin Drive, San Diego, Calif. 92121) and anti-glutathione peroxidase (GPx) IgG polyclonal antibodies (The Binding Site, Inc., 5889 Oberlin Drive, San Diego, Calif. 92121) dissolved in a hypotonic solution. After five minutes, a dip test strip with bound sheep anti-human SOD and anti-human GPx IgG polyclonal antibodies (The Binding Site, Inc., 5889 Oberlin Drive, San Diego, Calif. 92121) are inserted into test tube #2. After five minutes, the test strip is removed from the tube and rinsed with tap water.

The test strip is then dipped into a third test tube (tube #3), which contains the peroxidase substrate, hydrogen peroxide ($H_2O_2$) and diaminobenzidine (DAB); (Sigma Chemical Co., St. Louis, Mo. 63178). The color ratio of SOD/GPx will provide an indication of pregnancy potential by comparison with a chart provided with the kit. Color in the GPx pad indicates greater than 10 million motile sperm/mL. If the color in the SOD pad is higher than the color in the GPx pad, a high pregnancy potential of the sperm is indicated. If the color in the SOD pad is equal to or lower than the color in the GPx pad, a low pregnancy potential is indicated.

EXAMPLE 4

Temperature Stress for Predicting Pregnancy Potential of a Sperm Sample

Human sperm (HS) samples were obtained from 44 male partners of couples undergoing in vitro fertilization (IVF) (n=33) or gamete intrafallopian transfer (GIFT) (n=11). All male partners had normal semen by conventional analysis (By convention, a normal semen sample is defined as having greater than 20 million cells/mL, greater than 60% motility, a rate of progression greater than 2 (on a scale of 1 to 4), greater than 60% normal forms, 1.5 to 5.0 mL of ejaculate, no significant sperm agglutination, no significant number of leucocytes, and no hyperviscosity). HS samples were washed using the standard Percoll procedure and resuspended in HTF medium containing 10% plasmanate. An aliquot of the HS suspension was utilized for artificial reproductive technologies (ART, e.g. IVF and GIFT) and a 100 L aliquot of the same HS suspension was incubated at 40° C. for 4 h (stress test). Stress test (ST) scores were expressed as the ratio of final to initial motility. Analysis was performed by stepwise multiple regression. The independent variables were: women's age; HS motility before and after the ST; ST score; and the number of embryos transferred per IVF cycle. The dependent variables were: pregnancy and fertilization outcome.

In a blind cohort study, of the 44 ART cycles, 11 (25%) resulted in pregnancy. Of the 44 HS samples used in the study, 24 (55%) had ST scores $\leq 0.8$ and 20 (45%)>0.8. Controlling for all variables, the ST score was significantly correlated with pregnancy outcome (p.=0.0001). In sharp contrast, the motility before the ST was not correlated with pregnancy outcome. All pregnancies occurred in HS samples with ST scores >0.8. Therefore, a cut-off value >0.8 was selected to predict pregnancy outcome. The sensitivity of the ST was 100% and the specificity was 73%. The negative predictive value of the test, defined as the absence of pregnancy with ST scores <0.8, was 100% and the positive predictive value, defined as the occurrence of pregnancy with ST scores >0.8, was 55%. Although the ST score is highly predictive of pregnancy outcome, the fertilization rate was better predicted by the motility after the ST (p=0.007).

EXAMPLE 5

Oxidative Stress for Predicting Pregnancy Potential of a Sperm Sample

A similar test as described in Example 4 was carried out, except that the stress was provided by adding 10 μL of 0.125 mM ferrous iron in D-PBS (deionized-phosphate buffer saline) and 0.6 mM ascorbate also in D-PBS to 30 μL sperm suspensions for a total volume of 50 μL and incubating the mixture for 0.5 h at 37° C. with gentle shaking. Results indicate that the values obtained correlate with the ST score at 40° C. for 4 h.

Those skilled in the art will recognize, or be able to ascertain using no more than routine experimentation, many equivalents to the specific embodiments of the invention described herein. Such equivalents are intended to be encompassed by the following claims.

I claim:

1. A diagnostic assay for determining the contraceptive capacity of sperm in a sperm containing sample comprising the steps of:

a) isolating sperm from the sperm containing sample;

b) contacting the isolated sperm with detectably labeled antibodies specific for glutathione peroxidase to specifically bind the labeled antibodies to the isolated sperm;

c) measuring an amount of the labeled glutathione peroxidase antibodies bound specifically to the isolated sperm; and d) comparing the amount of bound labeled antibodies with an amount of detectably labeled glutathione peroxidase antibodies bound to a standard sample comprised of 10,000 motile sperm per milliliter, wherein when the amount of detectably labeled glutathione peroxidase antibodies specifically bound to the isolated sperm is greater than or equal to the amount of detectably labeled glutathione peroxidase antibodies bound to the standard sample, it is an indication that the isolated sperm has high pregnancy potential and when the amount of detectably labeled glutathione peroxidase antibodies specifically bound to the isolated sperm is less than the amount of detectably labeled glutathione peroxidase antibodies bound to the standard sample, it is an indication that the isolated sperm has low pregnancy potential.

2. A test kit for determining pregnancy potential of a sperm sample, comprising:

a) containers;

b) detectably labeled superoxide dismutase antibodies and detectably labeled glutathione peroxidase antibodies; and c) a standard indication for a concentration of superoxide dismutase indicative of high and/or low pregnancy potential and a standard indication for a concentration of glutathione peroxidase indicative of high and/or low pregnancy potential.

3. A test kit for determining fertilizing ability of a sperm sample, comprising:

a) a collection container;

b) a first container;

c) a dispensing device for delivering a defined volume of semen from the collection container into the first container;

d) a second container which includes detectably labeled superoxide dismutase antibodies and detectably labeled glutathione peroxidase antibodies;

e) a dispensing device for delivering a defined volume of semen from the first container into the second container; and f) a standard indication for a concentration of superoxide dismutase indicative of high and/or low pregnancy potential and a standard indication for a concentration of glutathione peroxidase indicative of high and/or low pregnancy potential.

4. A test kit of claim 3, which also includes at least one means reagent or device selected from the group consisting of: a means for removing contaminants from a semen sample, an enzyme reagent for accelerating semen liquefaction and a dispensing device.

5. The kit of claim 3, wherein the collection container is conformed to capture ejaculate.

6. The kit of claim 3, wherein the first container contains a solution for facilitating sperm swim-up.

* * * * *